(12) United States Patent
Hua

(10) Patent No.: US 10,406,351 B2
(45) Date of Patent: Sep. 10, 2019

(54) METHODS AND SYSTEMS FOR INTRAVENTRICULAR BRAIN STIMULATION

(71) Applicant: Sherwin Hua, Hillsborough, CA (US)

(72) Inventor: Sherwin Hua, Hillsborough, CA (US)

(*) Notice: Subject to any disclaimer, the term of this patent is extended or adjusted under 35 U.S.C. 154(b) by 0 days.

(21) Appl. No.: 15/891,231

(22) Filed: Feb. 7, 2018

(65) Prior Publication Data
US 2018/0229027 A1    Aug. 16, 2018

Related U.S. Application Data

(63) Continuation of application No. 14/266,732, filed on Apr. 30, 2014, now Pat. No. 9,919,146.

(60) Provisional application No. 61/818,312, filed on May 1, 2013.

(51) Int. Cl.
*A61N 1/05* (2006.01)
*A61N 1/36* (2006.01)

(52) U.S. Cl.
CPC .......... *A61N 1/0534* (2013.01); *A61N 1/0529* (2013.01); *A61N 1/36064* (2013.01); *A61N 1/36067* (2013.01); *A61N 1/36082* (2013.01)

(58) Field of Classification Search
None
See application file for complete search history.

(56) References Cited

U.S. PATENT DOCUMENTS

| | | | |
|---|---|---|---|
| 5,411,546 A | 5/1995 | Bowald et al. | |
| 5,531,779 A | 7/1996 | Dahl et al. | |
| 5,975,085 A | 11/1999 | Rise | |
| 6,176,242 B1 | 1/2001 | Rise | |
| 6,208,881 B1 | 3/2001 | Champeau | |
| 6,214,016 B1 | 4/2001 | Williams et al. | |
| 6,227,203 B1 | 5/2001 | Rise et al. | |
| 6,263,237 B1 | 7/2001 | Rise | |

(Continued)

FOREIGN PATENT DOCUMENTS

| EP | 1062973 | 12/2000 |
|---|---|---|
| WO | WO 2005/051306 | 6/2005 |

(Continued)

OTHER PUBLICATIONS

"Difference in Gameplay Mechanics Between Gold, Silver and Bronze" [online], Apr. 2, 2012 [retrieved Jan. 6, 2015]. Retrieved from the Internet <URL:http://forum.bioware.com/topic/309690-difference-in-gameplay-mechanicsbetween-gold-silver-and-bronze/>, 7 pages.

(Continued)

*Primary Examiner* — Brian T Gedeon
(74) *Attorney, Agent, or Firm* — Knobbe, Martens, Olson & Bear LLP

(57) ABSTRACT

The present application is directed to devices and methods that can treat dementia or other brain disorders via electrical stimulation. Embodiments disclosed herein utilize brain stimulation of brain areas involved in memory and cognition through an intraventricular approach. Brain stimulation is combined with CSF flow in an intraventricular electrode having one or more passageways to permit fluid to flow therethrough. For example, an intraventricular electrode shunt catheter can be safely placed in any part of the ventricular system and through any foramen or aqueduct of the ventricular system without fear of obstruction to CSF flow.

20 Claims, 12 Drawing Sheets

(56) References Cited

U.S. PATENT DOCUMENTS

| | | |
|---|---|---|
| 6,343,226 B1 | 1/2002 | Sunde et al. |
| 6,445,953 B1 | 9/2002 | Bulkes et al. |
| 6,665,562 B2 | 12/2003 | Gluckman |
| 6,764,498 B2 | 7/2004 | Mische |
| 6,896,618 B2 | 5/2005 | Benoy et al. |
| 6,978,180 B2 | 12/2005 | Tadlock |
| 7,150,737 B2 | 12/2006 | Purdy et al. |
| 7,209,787 B2 | 4/2007 | DiLorenzo |
| 7,277,758 B2 | 10/2007 | DiLorenzo |
| 7,295,875 B2 | 11/2007 | Wallace et al. |
| 7,386,350 B2 | 6/2008 | Villims |
| 7,440,806 B1 | 10/2008 | Whitehurst et al. |
| 7,493,171 B1 | 2/2009 | Whitehurst et al. |
| 7,515,961 B2 | 4/2009 | Germanson et al. |
| 7,684,867 B2 | 3/2010 | Jaax et al. |
| 7,725,196 B2 | 5/2010 | Machado et al. |
| 7,894,912 B2 | 2/2011 | Benabid et al. |
| 7,917,230 B2 | 3/2011 | Bly |
| 7,974,696 B1 | 7/2011 | DiLorenzo |
| 7,991,465 B2 | 8/2011 | Bartic et al. |
| 8,000,795 B2 | 8/2011 | Lozano |
| 8,052,711 B2 | 11/2011 | Hanse et al. |
| 8,060,207 B2 | 11/2011 | Wallace et al. |
| 8,103,350 B2 | 1/2012 | Wallace et al. |
| 8,147,328 B2 | 4/2012 | Carroll et al. |
| 8,150,524 B2 | 4/2012 | Maschino et al. |
| 8,209,027 B2 | 6/2012 | Butson et al. |
| 8,216,173 B2 | 7/2012 | Dacey, Jr. et al. |
| 8,246,466 B2 | 8/2012 | Herrmann et al. |
| 8,255,297 B2 | 8/2012 | Morgenstern et al. |
| 8,282,593 B2 | 10/2012 | Dacey, Jr. et al. |
| 8,287,383 B1 | 10/2012 | Etter et al. |
| 8,292,743 B1 | 10/2012 | Etter et al. |
| 8,296,781 B1 | 10/2012 | Lebaredian et al. |
| 8,328,642 B2 | 12/2012 | Mosites et al. |
| 8,333,753 B2 | 12/2012 | Nishtala |
| 8,343,086 B2 | 1/2013 | Dacey, Jr. et al. |
| 8,346,365 B2 | 1/2013 | Lozano |
| 8,348,747 B2 | 1/2013 | Arezina et al. |
| 8,360,870 B2 | 1/2013 | Herrmann et al. |
| 8,366,550 B2 | 2/2013 | Herrmann et al. |
| 8,366,652 B2 | 2/2013 | Dacey, Jr. et al. |
| 8,388,452 B2 | 3/2013 | Auterio et al. |
| 8,401,654 B1 | 3/2013 | Foster et al. |
| 8,417,345 B2 | 4/2013 | Machado et al. |
| 8,515,541 B1 | 8/2013 | Jaax et al. |
| 8,515,542 B2 | 8/2013 | Jaax et al. |
| 8,706,181 B2 | 4/2014 | Stypulkowski et al. |
| 8,731,674 B2 | 5/2014 | Wallace |
| 8,798,754 B2 | 8/2014 | Knudson et al. |
| 8,944,908 B1 | 2/2015 | Wakeford et al. |
| 9,307,925 B2 | 4/2016 | Russell et al. |
| 9,327,069 B2 | 5/2016 | Foster et al. |
| 9,352,145 B2 | 5/2016 | Whitehurst et al. |
| 9,421,373 B2 | 8/2016 | DiLorenzo |
| 9,630,019 B2 | 4/2017 | Valente et al. |
| 9,724,515 B2 | 8/2017 | Fostick et al. |
| 9,867,978 B1 | 1/2018 | Rapoport et al. |
| 9,919,146 B2 | 3/2018 | Hua |
| 9,919,148 B2 | 3/2018 | Howard et al. |
| 9,925,376 B2 | 3/2018 | Hartig et al. |
| 2003/0088245 A1 | 5/2003 | Woloszko et al. |
| 2003/0119581 A1 | 6/2003 | Cannon et al. |
| 2003/0135147 A1 | 7/2003 | Rosenberg et al. |
| 2005/0049649 A1 | 3/2005 | Luders et al. |
| 2005/0054439 A1 | 3/2005 | Rowe et al. |
| 2005/0076002 A1 | 4/2005 | Williams et al. |
| 2005/0113164 A1 | 5/2005 | Bueche et al. |
| 2005/0137646 A1 | 6/2005 | Wallace et al. |
| 2005/0203599 A1 | 9/2005 | Garabedian et al. |
| 2006/0025841 A1 | 2/2006 | McIntyre |
| 2006/0058854 A1 | 3/2006 | Abrams et al. |
| 2007/0004496 A1 | 1/2007 | Gordon et al. |
| 2007/0027498 A1 | 2/2007 | Maschino et al. |
| 2007/0060974 A1 | 3/2007 | Lozano |
| 2007/0066403 A1 | 3/2007 | Conkwright |
| 2007/0265683 A1 | 11/2007 | Ehrlich |
| 2008/0046012 A1 | 2/2008 | Covalin et al. |
| 2008/0182664 A1 | 7/2008 | Kaplan et al. |
| 2008/0200244 A1 | 8/2008 | Rowe et al. |
| 2008/0234034 A1 | 9/2008 | Tessmer et al. |
| 2008/0266250 A1 | 10/2008 | Jacob |
| 2008/0293466 A1 | 11/2008 | Arakawa et al. |
| 2008/0318668 A1 | 12/2008 | Ching et al. |
| 2009/0051114 A1 | 2/2009 | Robbers et al. |
| 2009/0054955 A1 | 2/2009 | Kopell et al. |
| 2009/0125080 A1 | 5/2009 | Montgomery |
| 2009/0181771 A1 | 7/2009 | Sogabe |
| 2009/0181774 A1 | 7/2009 | Ratcliff |
| 2009/0318232 A1 | 12/2009 | Harris |
| 2010/0144424 A1 | 6/2010 | Rodgers et al. |
| 2010/0166065 A1 | 7/2010 | Perlman et al. |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0249692 A1 | 9/2010 | Dacey, Jr. et al. |
| 2010/0279762 A1 | 11/2010 | Sohn et al. |
| 2010/0292629 A1 | 11/2010 | Dacey, Jr. et al. |
| 2010/0304839 A1 | 12/2010 | Johnson |
| 2011/0093361 A1 | 4/2011 | Morales |
| 2011/0106607 A1 | 5/2011 | Alfonso et al. |
| 2011/0112590 A1 | 5/2011 | Wu et al. |
| 2012/0009997 A1 | 1/2012 | Youm |
| 2012/0150695 A1 | 6/2012 | Fan et al. |
| 2013/0005437 A1 | 1/2013 | Bethke et al. |
| 2013/0014033 A1 | 1/2013 | Hamick et al. |
| 2013/0066695 A1 | 3/2013 | Just |
| 2013/0079082 A1 | 3/2013 | Bancel et al. |
| 2013/0079145 A1 | 3/2013 | Lam et al. |
| 2013/0085838 A1 | 4/2013 | Tennenholtz et al. |
| 2013/0289385 A1 | 10/2013 | Lozano et al. |
| 2014/0031129 A1 | 1/2014 | Morrison |
| 2014/0122720 A1 | 5/2014 | Jung et al. |
| 2014/0243714 A1 | 8/2014 | Ward et al. |
| 2014/0274308 A1 | 9/2014 | Guinn et al. |
| 2014/0278686 A1 | 9/2014 | Mullings |
| 2014/0357344 A1 | 12/2014 | Grier |
| 2014/0358651 A1 | 12/2014 | Koh et al. |
| 2015/0170455 A1 | 6/2015 | Rad |
| 2016/0158051 A1 | 6/2016 | Mische |
| 2016/0166326 A1 | 6/2016 | Bakker et al. |
| 2016/0220821 A1 | 8/2016 | O'Connell et al. |
| 2016/0228693 A1 | 8/2016 | Vardiman |
| 2016/0331971 A1 | 11/2016 | Gill |
| 2016/0367809 A1 | 12/2016 | Patel et al. |
| 2017/0143966 A1 | 5/2017 | Reymers et al. |
| 2017/0151436 A1 | 6/2017 | Flaherty et al. |

FOREIGN PATENT DOCUMENTS

| | | |
|---|---|---|
| WO | WO 2006/015087 | 2/2006 |
| WO | WO 2006/099462 | 9/2006 |
| WO | WO 2007/002144 | 1/2007 |
| WO | WO 2008/149289 | 12/2008 |
| WO | WO 2011/133583 | 10/2011 |
| WO | WO 2014/159757 | 10/2014 |
| WO | WO 2014/210286 | 12/2014 |
| WO | WO 2017/039762 | 3/2017 |

OTHER PUBLICATIONS

PCT International Preliminary Report on Patentability for PCT/US2014/044297, dated Jan. 7, 2016, 6 pages.

Hewitt, John, Rise of the Cyborgs , https://www.extremetech.com/extreme/144579-rise-of-the-cyborgs, Exteme Tech, Jan. 14, 2013, in 6 pages.

(56) References Cited

OTHER PUBLICATIONS

Koivisto, A.M. et al (2013) Poor Cognitive Outcome in Shunt-Responsive Idiopathic Normal Pressure Hydrocephalus. Neurosurgery 72(1):1-8.

Laxton, et al (2013) Deep Brain Stimulation for the Treatment of Alzheimer Disease and Dementias. World Neurosurgery 80 (3/4), S28.e1-8.

Torres, et al. (2012) Body Fat and Body Weight Reduction Following Hypothalamic Deep Brain Stimulation in Monkeys: an Intraventricular approach, International Journal of Obesity, Feb. 21, 2012, pp. 1537-1544.

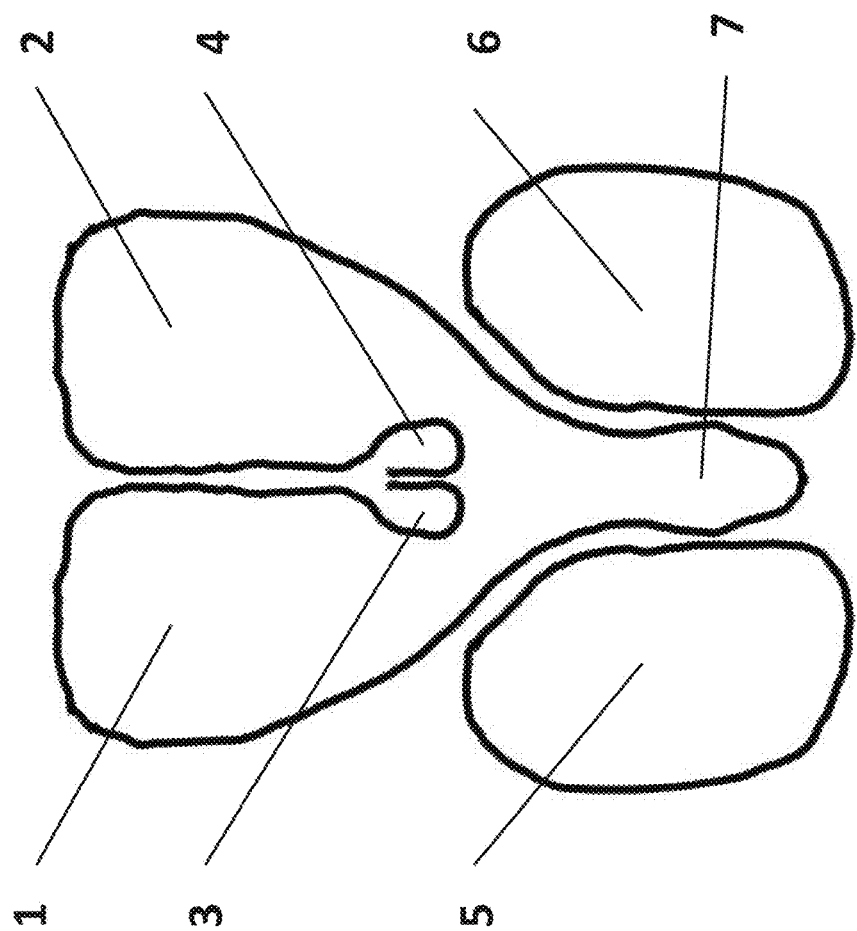

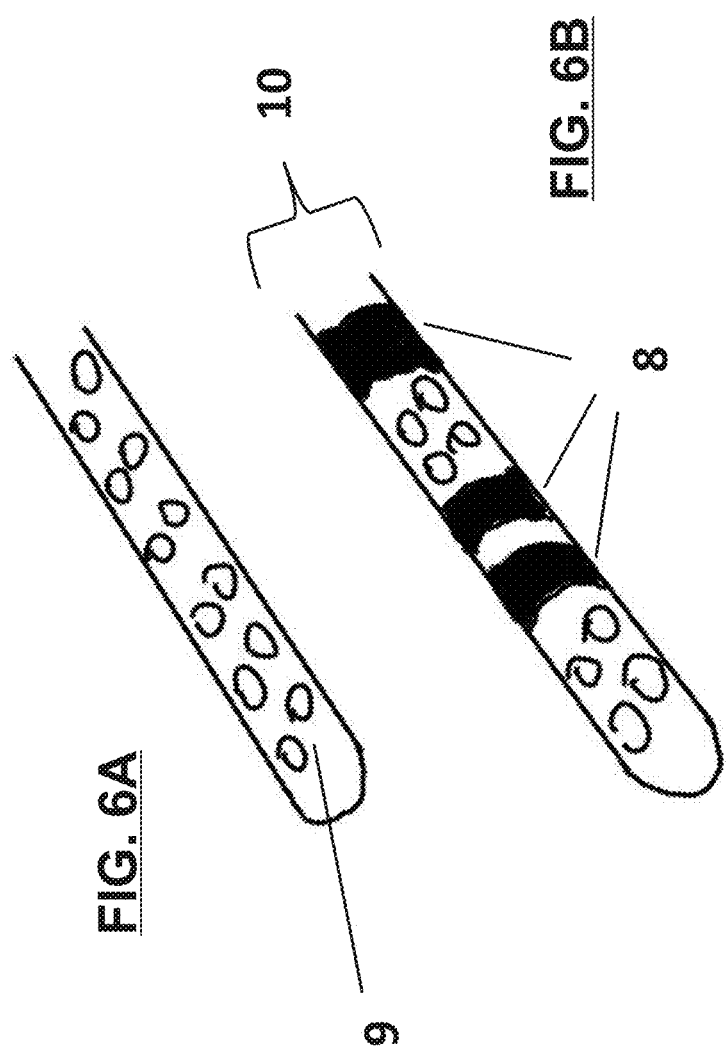

METHODS AND SYSTEMS FOR INTRAVENTRICULAR BRAIN STIMULATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.5

BACKGROUND

Field

This disclosure relates to methods and systems for treatment of neurological disorders, and particularly for treating brain disorders using electrodes.

Description of the Related Art

Brain stimulation has been shown to be effective for the treatment of Parkinson's Disease and other movement disorders, Epilepsy, and Depression. Brain stimulation has the potential to be an effective treatment for numerous other disorders. Recently brain stimulation has been shown to be effective in enhancing memory when targeted at a component of the Papez circuit, a memory circuit of the brain, including the hippocampus, fornix, anterior thalamus etc. Clinical trials have been initiated to investigate fornix stimulation for Alzheimer's disease and its precursor, mild cognitive impairment (MCI). Furthermore, Lozano has also proposed stimulation of the anterior nucleus of the thalamus as another target for Alzheimer's disease and MCI.

Idiopathic Normal Pressure Hydrocephalus (NPH) is another neurological disorder that may be related to dementia, MCI, and Alzheimer's disease. NPH, however, is treated differently than the proposed treatment for MCI and Alzheimer's disease. The mainstay of treatment for NPH is the use of a ventricular shunt to divert cerebral spinal fluid (CSF) to the peritoneum, atrium, or pleural space. It is thought that the size of the ventricles in NPH is greater than the expected ventricular enlargement due to brain atrophy called hydrocephalus ex vacuo. By draining CSF, the size of the ventricles can be reduced and pressure on specific sensitive areas of the brain is thought to be reduced. NPH is typically associated with a triad of clinical symptoms, namely memory loss, gait instability, and urinary incontinence. Ventricular shunts have been shown to improve all three components of the clinical triad but are most successful and effective for gait and least effective for memory and cognitive changes. It has been proposed that NPH is an entity belonging to a spectrum of dementias. A recent study by Koivisto et al. (*Poor Cognitive Outcome in Shunt-Responsive Idiopathic Normal Pressure Hydrocephalus*. Neurosurgery 72(1):1-8 (2013)) demonstrated that while the diagnosis of NPH was not initially associated with dementia, a high number of patients with NPH that were treated with ventricular shunts later developed dementia including Alzheimer's disease. Given this association of NPH with dementia and Alzheimer's disease, it seems that the use of ventricular shunting for NPH is not effective in preventing the development of dementia and dementia related symptoms such as memory and cognitive decline in these patients.

SUMMARY

In accordance with one aspect of the present disclosure, there is provided a neuromodulation system configured to pass into, within, or through a ventricle in the brain, the system comprising one or more passageways for fluid; and an electrode or effector configured to modulate neural activity thereby modulating a neural state.

In some embodiments, the neural activity modulated can come from brain cells or neural fibers. In some embodiments, the neural activity can be at the fornix, the thalamus, the anterior nucleus of the thalamus, the circuit of Papez, and/or the hypothalamus. In some embodiments, the neural state can be an abnormal neural state, a seizure, epilepsy, Alzheimer's disease, Mild Cognitive Impairment, a normal neural state, Attention Deficit and Hyperactivity Disorder, stroke, multiple sclerosis, Parkinson's Disease, neural degenerative disease, cerebral palsy, schizophrenia, neuropsychiatric disorder, encephalopathy, and/or normal pressure hydrocephalus. In some embodiments, modulation of neural activity can comprise an increase in neural activity, a decrease in neural activity, and/or can lead to modulation of memory, attention, or concentration. In some embodiments, perforations in the passageway can permit cerebral spinal fluid to flow therethrough. In some embodiments, the perforations can be proximal to the electrode or effector, or distal to the electrode or effector, or both proximal and distal to the electrode or effector. In some embodiments, the electrode or effector is configured to pass through the foramen of Monroe. In some embodiments, the passageway can permit cerebrospinal fluid to flow out of the cranium to a reservoir. In some embodiments, the passageway is configured to permit cerebrospinal fluid to flow out of the cranium to a drain in a body cavity including the circulatory system, peritoneum, or pleural space, and wherein the passageway comprises a shunt. In some embodiments, the passageway is part of a shunt system with a valve controlling cerebrospinal fluid flow. In some embodiments, the passageway is configured so as to not be open to cerebrospinal fluid flow outside the cranium. In some embodiments, the passageway is configured to allow materials such as drugs, proteins, genes, viruses, particles, molecules, enhancers, etc. to flow into the ventricle. In some embodiments, the passageway comprises multiple compartments and is configured to allow bidirectional flow of fluid or materials. In some embodiments, the system can further include a controlled delivery pump to deliver materials through the passageway. In some embodiments, the passageway comprises an outer and inner surface forming a lumen. In some embodiments, the passageway comprises multiple lumens that are not enclosed similar to a Blake drain with an "X" or starfish cross sectional pattern. In some embodiments, the electrode or effector is located near an outer surface on the cross section of the catheter passageway to affect neural tissue. In some embodiments, the tip of the electrode or effector is curved to conform to the contour of the ventricular wall to reach the target neural structure. In some embodiments, the curved electrode or effector tip reaches both fornices by curving from one foramen of Monroe past the ipsilateral fornix to the contralateral fornix. In some embodiments, the system is configured to allow the electrode or effector to reach both the fornix and anterior nucleus of thalamus. In some embodiments, the electrode or effector is carried by a catheter, and wherein the catheter has adherence properties to maintain contact with neural structures on the wall of the ventricle. In some embodiments, the electrode or effector is carried by a catheter, and wherein the catheter uses mechanical properties to maintain contact with neural structures on the wall of the ventricle or foramen of Monroe. In some embodiments, the electrode or effector is carried by a catheter, and wherein the catheter diameter can be enlarged or decreased to better fit within the ventricle or foramen of Monroe so that the electrode or effector is in better contact with the neural structures on the wall of the ventricular system. In some embodiments, the electrode or effector is carried by a catheter, and wherein the catheter is inserted to the target using stereotactic guidance. In some embodiments, the electrode or effector is carried by a catheter, and wherein the catheter is inserted to the target using an endoscopic viewer. In some embodiments, the catheter or lumen is inserted to the target using fluoroscopic visualization guided by radio-opaque substance.

In accordance with another aspect, there is provided a neuromodulation system comprising one or more electrodes configured for intraventricular brain stimulation, and means for allowing cerebral spinal fluid flow during intraventricular placement of the one or more electrodes.

In some embodiments, the means for allowing cerebral spinal fluid flow can include a shunt catheter. In some embodiments, the means for allowing cerebral spinal fluid flow comprises one or more passageways. In some embodiments, the means for allowing cerebral spinal fluid flow comprises a Blake drain.

In accordance with another aspect, there is provided a method of modulating neural activity, the method comprising: providing a shunt electrode comprising an electrode and a passageway for fluid flow through the shunt electrode; inserting the shunt electrode into a brain; and modulating neural activity in the brain with the shunt electrode.

In some embodiments the neural activity modulated comes from brain cells or neural fibers. In some embodiments, the neural activity modulated is at the fornix, at the thalamus, at the anterior nucleus of the thalamus, within the circuit of Papez, and/or the hypothalamus. In some embodiments, prior to the modulating, the neural activity is in an abnormal state. In some embodiments, the abnormal neural state can be a seizure, epilepsy, Alzheimer's disease, Mild Cognitive Impairment, Attention Deficit and Hyperactivity Disorder, and/or encephalopathy. In some embodiments, prior to the modulating, the neural activity is in a normal neural state. In various embodiments, the modulation of neural activity can include an increase in neural activity, a decrease in neural activity, modulation of memory attention, or concentration. In some embodiments, perforations in the passageway permit cerebral spinal fluid to flow therethrough. In some embodiments, the passageway has perforations proximal to the electrode. In some embodiments, the passageway has perforations distal to the electrode. In some embodiments, the passageway has perforations both proximal and distal to the electrode for cerebrospinal fluid flow between compartments proximal and distal to the electrode. In some embodiments, the method includes inserting the shunt electrode through the foramen of Monroe In some embodiments, the passageway is configured to permit cerebrospinal fluid to flow out of the cranium to a reservoir. In some embodiments, the passageway is configured to permit cerebrospinal fluid to flow out of the cranium to a drain in a body cavity including the circulatory system, peritoneum, or pleural space. In some embodiments, the passageway includes a valve for regulating flow therethrough. In some embodiments, the passageway is configured so as to not be open to cerebrospinal fluid flow outside the cranium. In some embodiments, the method further includes flowing one or more of the following materials into the ventricle through the passageway: drugs, proteins, genes, viruses, particles, molecules, or enhancers. In some embodiments, the passageway comprises multiple compartments and allows bidirectional flow of the one or more materials. In some embodiments, the method further includes actively pumping the one or more materials through the passageway. In some embodiments, the passageway comprises an outer and inner surface forming a lumen. In some embodiments, the passageway comprises multiple lumens that are not enclosed. In some embodiments, the electrode is located near an outer surface of the shunt electrode. In some embodiments, the tip of the shunt electrode is curved to conform to the contour of the ventricular wall to reach the target neural structure. In some embodiments, the curved electrode or effector tip reaches both fornices by curving from one foramen of Monroe past the ipsilateral fornix to the contralateral fornix. In some embodiments, the shunt electrode comprises a catheter, wherein the catheter uses mechanical properties to maintain contact with neural structures on the wall of the ventricle or foramen of Monroe. In some embodiments, the shunt electrode comprises a catheter, and wherein the catheter diameter can be enlarged or decreased to better fit within the ventricle or foramen of Monroe so that the electrode or effector is in better contact with the neural structures on the wall of the ventricular system. In some embodiments, the shunt electrode comprises a catheter, and wherein the shunt electrode is inserted into the site in the brain using target stereotactic guidance.

BRIEF DESCRIPTION OF THE DRAWINGS

FIG. 5 is a schematic diagram of the ventricular system.

FIGS. 6A and 6B illustrate shunt and electrode catheters, respectively.

DETAILED DESCRIPTION

Figure 1:
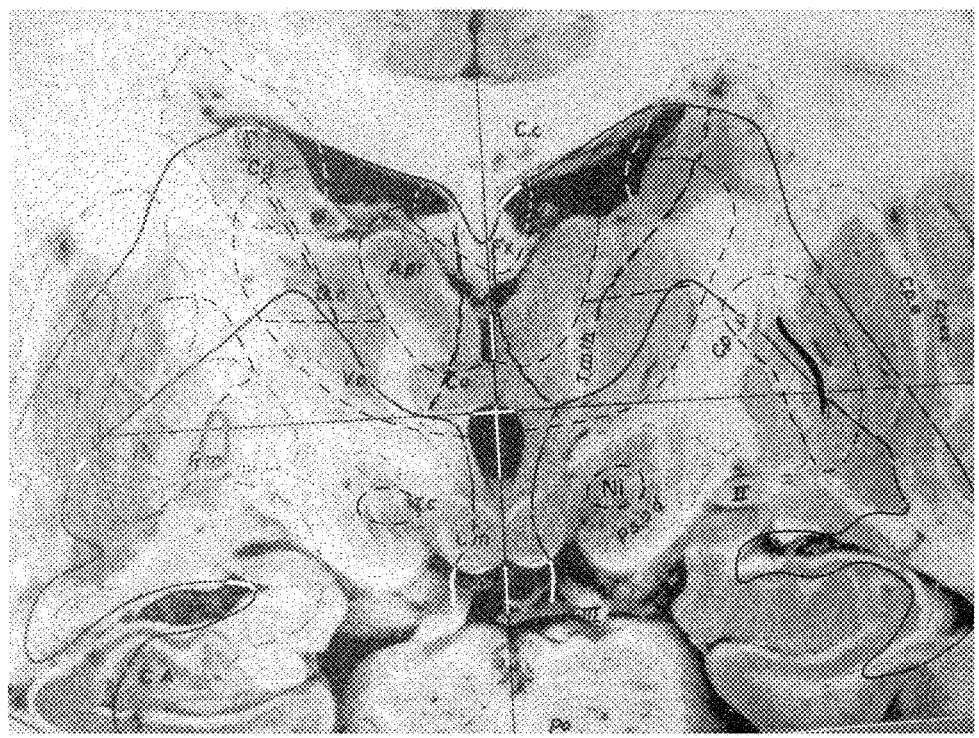
FIGS. 1-4 illustrate different views of a portion of the brain, including the fornix (Fx) and the anterior thalamic nucleus (A.pr), separated by the foramen of Monroe (Fo.M).
Figure 2:
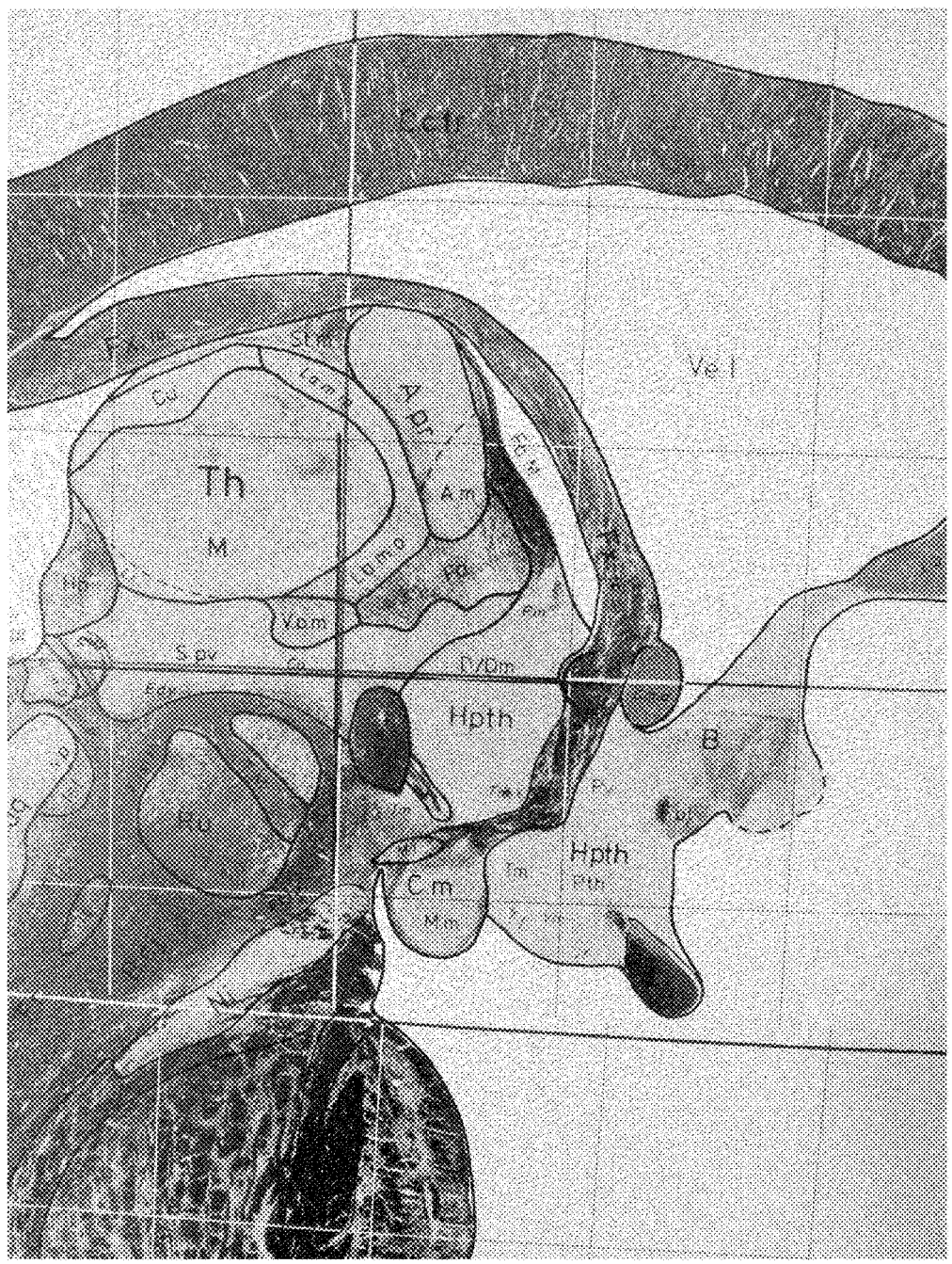
Figure 3:
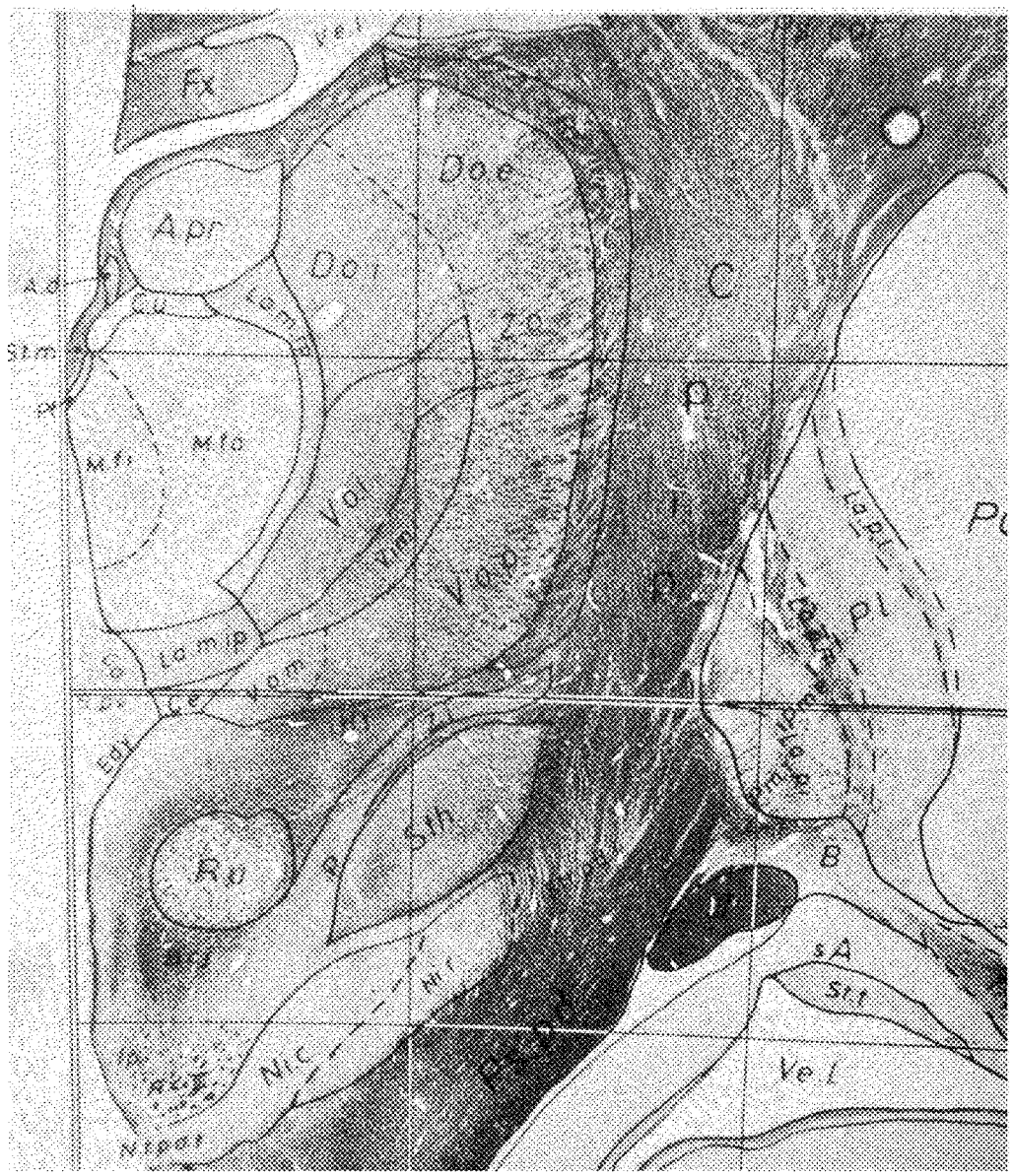
Figure 4:
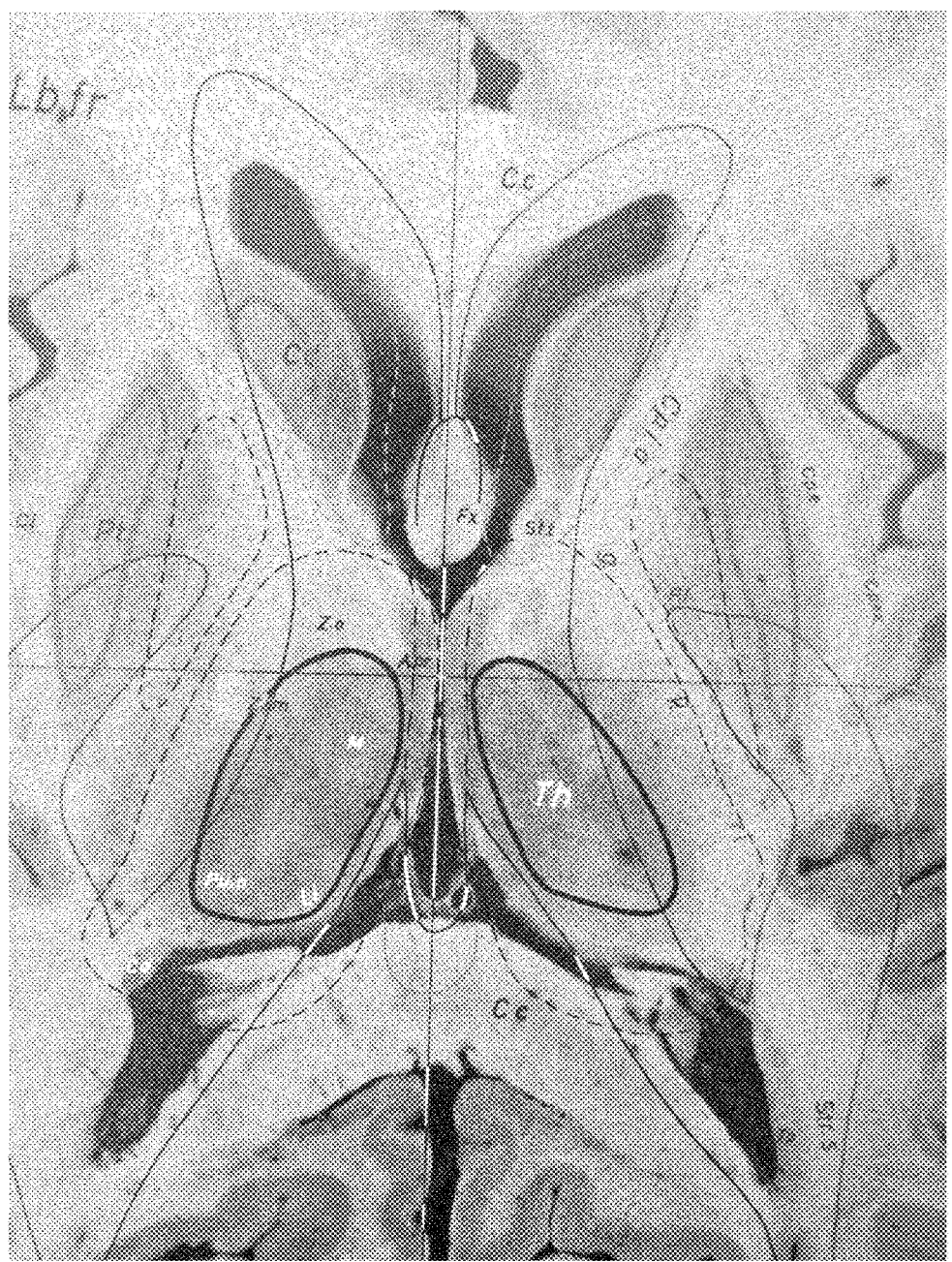

The following detailed description presents various descriptions of specific embodiments of the invention. However, the invention can be embodied in myriad different ways as defined and covered by the claims as presented herein and as may be presented in the future.

Disclosed herein are devices and methods that can treat dementia in a manner that is safer than the current stimulation strategy for Alzheimer's disease and provides improved therapy for patients with NPH. Embodiments disclosed herein utilize brain stimulation of brain areas involved in memory and cognition through an intraventricular approach. In one embodiment, by combining the advantages of both brain stimulation and CSF flow in an intraventricular electrode having one or more passageways to permit fluid to flow therethrough. For example, an intraventricular electrode shunt catheter can be safely placed in any part of the ventricular system and through any foramen or aqueduct of the ventricular system without fear of obstruction to CSF flow. This combined approach has applicability to not only memory and cognitive related brain disorders such as Alzheimer's disease, NPH, MCI, but also epilepsy and seizures as well as neuropsychiatric disorders as well.

One strategy for the treatment of Alzheimer's disease using brain stimulation involves targeting the fornix bilaterally through bilateral deep brain stimulation. The targets chosen require placement of deep brain stimulation electrodes through brain parenchyma close to delicate areas such as the hypothalamus. In contrast, the placement of ventricular shunts involve the placement of a ventricular shunt catheter through a shorter and safer stretch of cortical brain tissue to access the ventricle near the foramen of Monroe, which is the junction or portal between the lateral ventricle and the third ventricle. The ventricular system of older individuals with brain atrophy typically is enlarged due to ex vacuo dilatation. This enlargement allows easy access to the ventricle and intraventricular structures. Brain atrophy also makes accurate placement of deep brain stimulation electrodes into intraparenchymal targets less accurate due to brain shift and brain sag during surgery thus raising the risk of complications. Thus an intraventricular approach optimizes the fortuitously large ventricles in these patients while avoiding the risks and complications associated with placing electrodes within neural tissue, particularly near eloquent and important areas such as the hypothalamus and thalamus and in more fragile tissue of the atrophic brain.

The fornix, a key relay structure in the memory circuit and the main output pathway of the hippocampus, converges to form the roof of the foramen of Monroe. At this location the fornix of both sides come close together and run side by side. Thus this is an ideal target in some embodiments for brain stimulation because a single unilateral electrode can stimulate the fornix bilaterally at this location.

The difficulty with intraventricular brain stimulation of the fornix at the foramen of Monroe (FM) is that the foramen of Monroe is a small portal through which the cerebral spinal fluid made in the lateral ventricles traverse to drain into the third ventricle. If the FM is blocked or occluded, the patient could develop obstructive hydrocephalus, a potentially lethal condition. Thus a deep brain stimulation electrode placed in or near the fornix may lead to obstruction of the FM through scarring of tissues and choroid around the electrode.

One of the approaches disclosed herein is to combine the brain stimulation electrode with a ventricular shunt allowing cerebral spinal fluid flow through the novel brain stimulation electrode. In this manner the electrode can be placed through the FM from the lateral ventricle into the third ventricle. The electrode can also sit within the FM. Since the fornix from both sides of the brain come together to meet side by side near the FM, stimulation of both fornices can be accomplished by a single unilateral electrode at the FM or in the third ventricle. Additionally, the electrode components can be embedded not only within the shunt lumen but also can be placed within the wall of the shunt catheter, wherein the electrode components are then closer to the white matter tissue and brain tissue by being on the outer surface of the electrode-catheter. Furthermore, the shunt catheter diameter can be chosen or adjusted to "fit" into the size of the FM without fear of blocking the flow of CSF. By fitting the size of the shunt, the electrode components within the shunt catheter or the wall of the shunt catheter are then brought closer to the neural tissue near the surface of the ventricle such as the fornix, fornices, thalamus, hypothalamus, hippocampus, etc, then stimulation of the neural elements is more effective.

Stenting electrodes similar to those designed for cardiac pacing and defibrillation through an intravascular approach are also applicable in this situation with or without a shunt pathway for CSF diversion. One preferred embodiment is a stent electrode system that allows free CSF flow through the electrode system. Multiple designs for intravascular stenting electrodes have been proposed for cardiac and intravascular stimulation. Such embodiments can be applied to the intraventricular context, particularly in a trans-foramen of Monroe placement. These embodiments include wire electrodes that have a loose spring and are released upon removal of an outer carrier/introducer tube or device. Another embodiment is a mesh that expands when released from a carrier/introducer.

Another embodiment includes a blind shunt catheter that allows drainage and CSF flow between the different parts of the ventricular system that the electrode catheter is placed within and between. The term "blind" is used because in this case, CSF is not diverted out of the cranium, only between different intracranial compartments. An example of this placement is the foramen of Monroe and the blind shunt catheter portion would allow communication between the lateral and third ventricles, having passageways for CSF flow both in the area distal and proximal to the electrode situated in the foramen of Monroe.

Figure 7B:
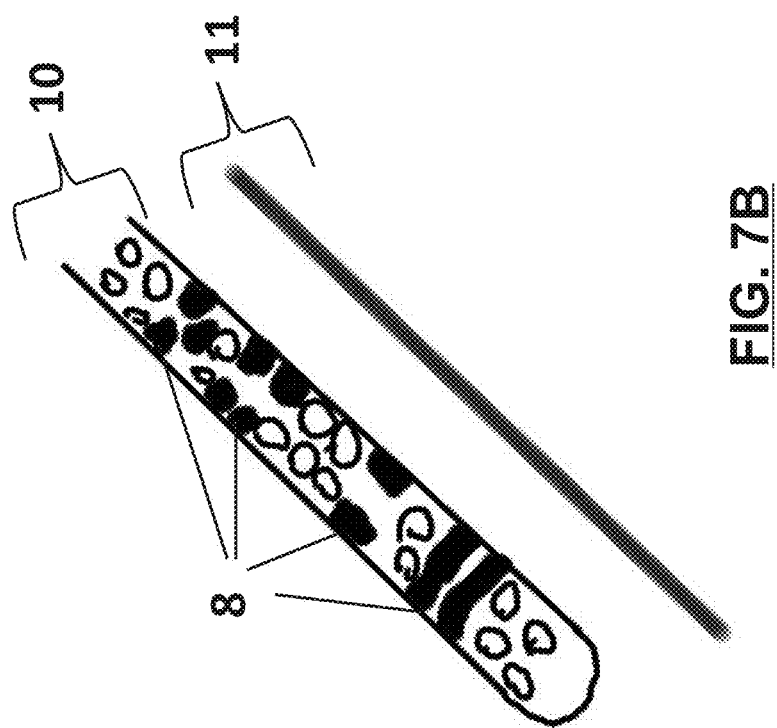
FIGS. 7A and 7B illustrate an electrode catheter in curved and straight configurations, respectively.
Figure 7A:
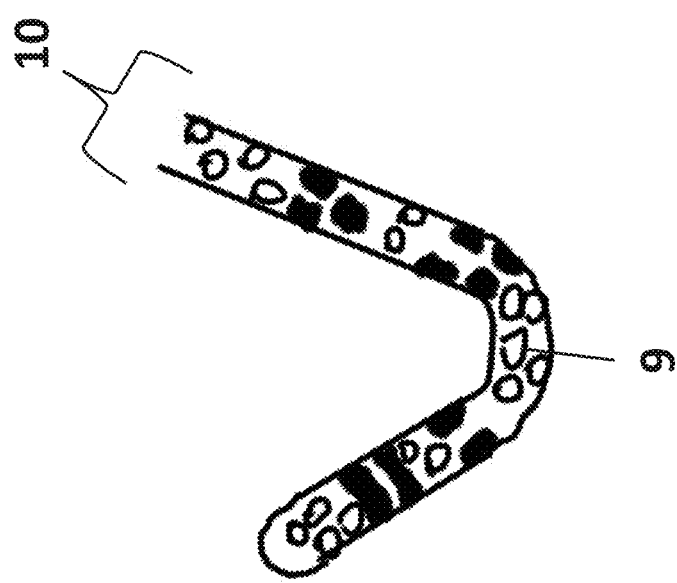

The tip of the catheter electrode preferably also has a shape that can curve through the FM of the ipsilateral side into the third ventricle and sit underneath both fornices. In some embodiments, the curve can be built into the shunt or electrode catheter and elicited when a straight guidewire is removed as shown in FIG. 7A and FIG. 7B. Alternatively the curve can be shapened or customized on an individual basis during the insertion process to customize the curvature to each individual's anatomy, in order to access both fornices. Bendable and malleable materials such as nitinol, which changes shape based on temperature or other conditions, e.g. electrical charge, or mechanical manipulation, is ideal for such applications to customize the curvature of the electrode within the ventricle. Precurved or preshaped catheter shapes that are inserted using a straight inner stylet also permit straight placement through the cortex, ventricle and foramen of Monroe, and once the catheter near final position through the foramen of Monroe, the natural curve can be "released" by removing the inner stylet.

Normal electrodes such as those used for deep brain stimulation (DBS) implanted into brain parenchyma cannot be bent or curved especially during the process of insertion or after insertion because any change in shape may cut, damage, compress, and/or destroy the brain tissue surrounding the tip. However since the shunt/electrode can be disposed within the ventricular system where cerebral spinal fluid (CSF) resides, only CSF will be displaced with alterations of the tip or shaft of the shunt electrode catheter.

Typically straight electrodes such as the DBS electrode or electrodes with a constant shape are placed stereotactically through predefined trajectories and paths based on a frame-based or frameless stereotactic system. Frameless systems, which allow minor changes during electrode placement, still are limited in the amount of change in trajectory after insertion through brain or neural tissue because any significant change may cause damage to neural tissue by slicing through the brain or compressing the brain tissue. In contrast, intravascular or endovascular procedures such as vascular stenting, cardiac angioplasty and stenting, and brain coiling of aneurysm and treatment of AVM's use a nonstereotactic freehand approach. These endovascular techniques use radiographic contrast material under fluoroscopic guidance to guide the catheter tip through the different venous or arterial branches to reach the target. Embodiments of the present invention allow both a stereotactic approach in the planning of the trajectory into the ventricular system and near the FM, but also allow a freehand intraventricular guidance by contrast medium under fluoroscopy similar to endovascular approaches. This fluoroscopic guidance is possible because venticulography has been a standard method used for localization of structures around the ventricles. In fact, ventriculography was the main method of localization in the brain before CT and MRI scans were developed. Thus using intraventricular fluoroscopic guidance, the shunt electrode catheter can be placed through the FM and into the third ventricle and even through the FM on the contralateral side. Also the shunt electrode catheter can be used to access any surface of the lateral or third ventricle. Some cases of intraventricular guidance through the aqueduct of sylvius into the fourth ventricle have been reported as well. Thus this cannulation of the aqueduct of sylvius by a shunt electrode catheter is applicable with embodiments of the current invention as well.

In addition to fluoroscopic guidance, endoscopy is also commonly used for intraventricular procedures such as third ventriculostomy, resection of colloid cysts, and intraventricular tumors. Thus, endoscopic guidance of the shunt electrode catheter allows precise placement of the catheter through the FM into nearly any surface of the lateral, third, and fourth ventricles. Preferably, the stylet within the shunt electrode catheter is equipped for endoscopic visualization, e.g., it is an endoscope or has a miniature camera on the tip such as a CCD camera, chip on the tip. This way when the electrode catheter is ideally placed, the endoscopic viewer (e.g., the endoscope or camera on the tip of the stylet) can be removed. The ventricular dilatation usually seen in patients with atrophy is advantageous for endoscopic approach through the ventricular system.

Placing electrodes within the ventricular system or along the wall of the ventricle requires the electrodes to be adhered to the ventricular wall, either by an adhesive or by a mechanical device. The adherence is preferably achieved by use of the hydrophobic and lipophilic properties of materials to adhere to neural tissue along the wall of the ventricular system. Other mechanisms for adhesion include mechanical adhesion, chemical adhesion, dispersive adhesion, electrostatic adhesion, and diffusive adhesion. One skilled in the art will recognize preferable methods to adhere an electrode onto the wall of the ventricle. However one advantage of embodiments of the present invention is to utilize the FM as an anchoring site for the electrode shunt catheter. Because of the shunting capability, obstruction to CSF flow is prevented and the electrode shunt catheter can use at least mechanical adhesion to contact and stay in contact with a particular ventricular surface.

Furthermore, the anterior thalamic nucleus makes up the lateral wall of the inferior FM and third ventricle. The anterior thalamus has been a target for not only epilepsy but also Alzheimer's disease and other cognitive disorders such as mild cognitive impairment (MCI). Thus an accurately placed electrode shunt catheter can access both the fornix and the anterior thalamus through an intraventricular approach that spares damage to the nuclei. This approach is advantageous because the anterior thalamic nucleus is difficult to access because it is typically shielded by the lateral ventricle and thus typical electrode placements into the anterior nucleus pass through the ventricle as well as a plexus of blood vessels near the ventricular walls. Thus an intraventricular access to the anterior nucleus requires only an entry into the ventricle at a safe entry point, i.e., that used for shunt catheter placement, and eliminates a second ventricular wall penetration required for typical anterior thalamic nucleus access. Other targets accessible from an intraventricular approach include but are not limited to the following: fornix, thalamus, anterior nucleus of thalamus, medial dorsal thalamic nucleus, anterior commissure, posterior commissure, mammillary bodies, hypothalamus.

Specifically, since the fornices comprise the superiomedial and anteriomedial walls of the FM, the electrode shunt catheter placed through the FM is ideally situated to interact with the FM. This interaction can include electrical stimulation or electrical recording. Other methods of interaction include cooling or heating, electrical field generation and stimulation, opticogenetic methods, laser methods, fluorescence methods, ultrasonic methods, direct electrical current stimulation, and mechanical stimulation or disruption. Since the fornix is the main output pathway of the hippocampus and a main fiber tract for circuit of Papez, stimulation and recording here is beneficial for treating a number of disorders including memory dysfunction such as Alzheimer's Disease, Normal Pressure Hydrocephalus, epilepsy, and depression. Accessing the fornix through an intraventricular approach is safer than the traditional direct intraparenchymal approach because the electrode currently passes through brain tissue throughout the entire tract and often through or close to important structures such as the hypothalamus. Instead, the intraventricular approach only passes through a small region of brain tissue, in the same safe manner that ventricular shunts are placed, with minimized risk to the deeper critical brain areas. Also, an intraventricular approach to the fornix at the area of the FM allows both fornices to be accessed using a unilateral approach, thereby eliminating half of the risk of the surgery, i.e. drilling a second burrhole and passing a second electrode on the contralateral side.

FIGS. 1-4 illustrate different views of a portion of the brain, including the fornix (Fx) and the anterior thalamic nucleus (A.pr), separated by the foramen of Monroe (Fo.M). FIG. 5 is a schematic diagram of the ventricular system showing right (1) and left (2) lateral ventricles, right (3) and left (4) fornices, third ventricle (7), and right (5) and left (6) thalami.

FIGS. 6A and 6B illustrate a straight shunt (FIG. 6A) and electrode catheter (FIG. 6B). FIG. 6A shows a typical shunt cather or ventriculostomy catheter that is a hollow tube with perforations (9). The perforations (9) allow drainage of CSF through the hollow tube or channel to the shunt and distal drainage site (usually the peritoneum, atrium of the heart, or pleural cavity). FIG. 6B shows a combination electrode catheter (10) system with electrodes embedded into a catheter with perforations similar to a shunt catheter such that CSF can flow from one ventricle to another while the electrode contacts (8) are near a site nearby the ventricular system such as the fornix and thalamus. The perforations prevent blockage of CSF flow when the electrode catheter passes through the foramen of Monroe.

Figure 8:
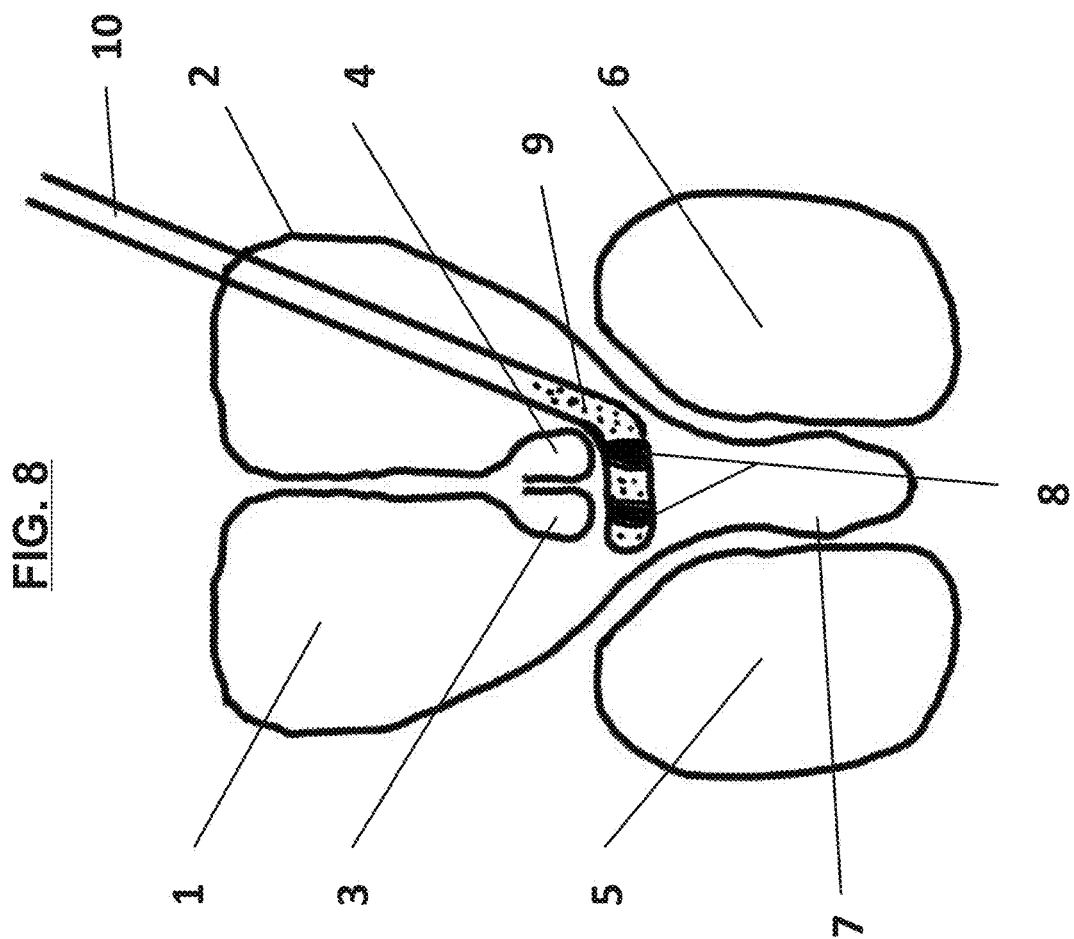
FIG. 8 illustrates a ventricular catheter electrode inserted into the brain.
Figure 9:
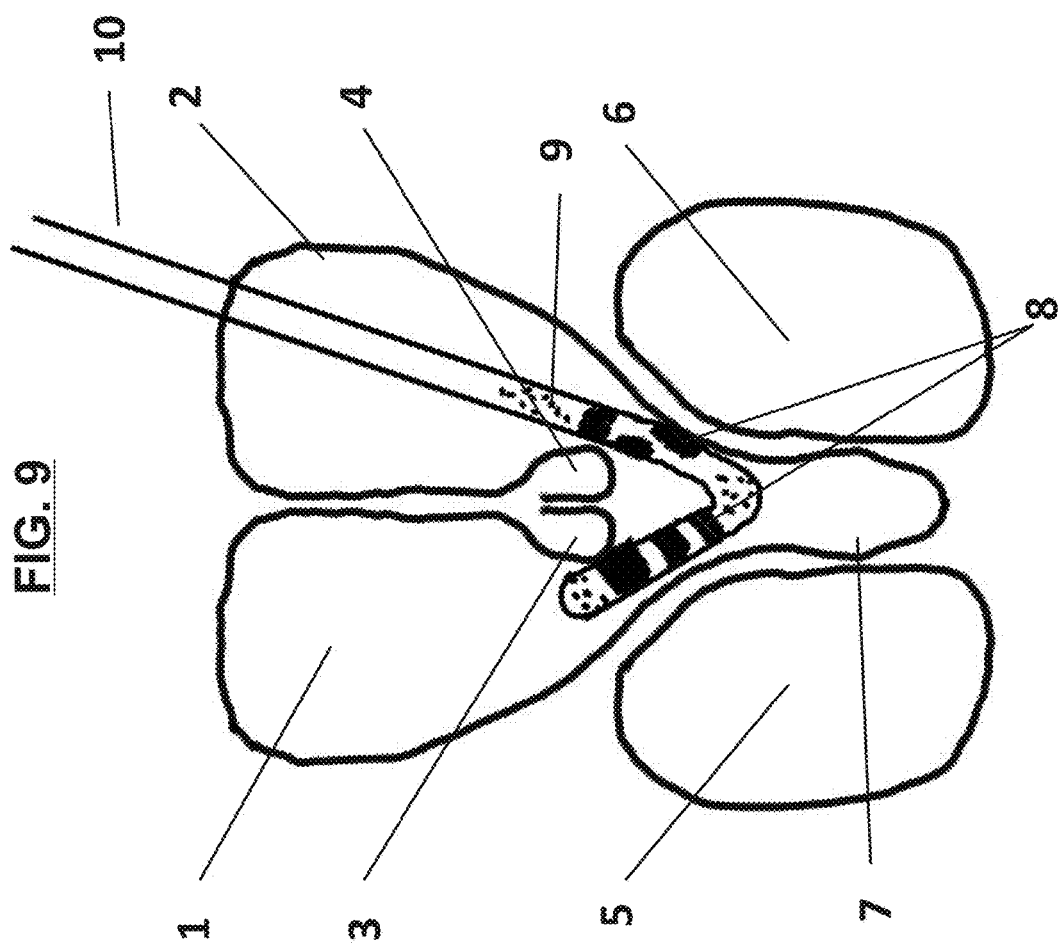
FIG. 9 illustrates a "V" curved ventricular electrode catheter inserted into the brain.

FIG. 7 illustrates one embodiment of a curved electrode catheter. As illustrated, an electrode catheter (10) can be preshaped into a bent configuration so that the electrode catheter can pass through one lateral ventricle through the foramen of Monroe into the third ventricle to the contralateral lateral ventricle through the contralateral foramen of Monroe. FIG. 7B shows that a straight rigid stylet (11) can be inserted into the lumen of the electrode catheter to straighten the prebent, naturally curved electrode during insertion. As the electrode is placed through the foramen of Monroe into the third ventricle, the stylet is pulled back and the prebent shape of the electrode naturally curves into the opposite foramen of Monroe into the contralateral lateral ventricle, as shown in FIGS. 8 and 9. The electrodes (8) shown can be both circumferential around the catheter or localized and distributed around the catheter for more focused current steering capabilities.

FIG. 8 illustrates the ventricular catheter electrode (10) passing through the left ventricle (2) and entering the third ventricle (7) through the foramen of Monroe (not lumbered). The electrode catheter (10) is curved under the left (4) and right (3) fornices. Perforations (9) allow free flow of CSF between the right ventricle (1), left ventricle (2), third ventricle (7) and shunt catheter (10). Electrodes (8) allow stimulation and interaction with both left (4) and right (3) fornices through a single passage of the electrode catheter through a single burrhole and a single side.

FIG. 9 illustrates one embodiment of a "V" curved ventricular electrode catheter (10). The sharper bend allows electrode contacts (8) to access the left fornix (4), right fornix (3), left thalamus (6), and right thalamus (5) all through a single electrode catheter and a single burrhole on a single side. The perforations (9) allow free CSF flow through the left ventricle (2), right ventricle (1), and third ventricle (7). The shunt catheter (10) also allows CSF to drain outside the cranium as in a ventriculo-peritoneal (-atrial or -pleural) shunt when CSF diversion is necessary.

Figure 10:
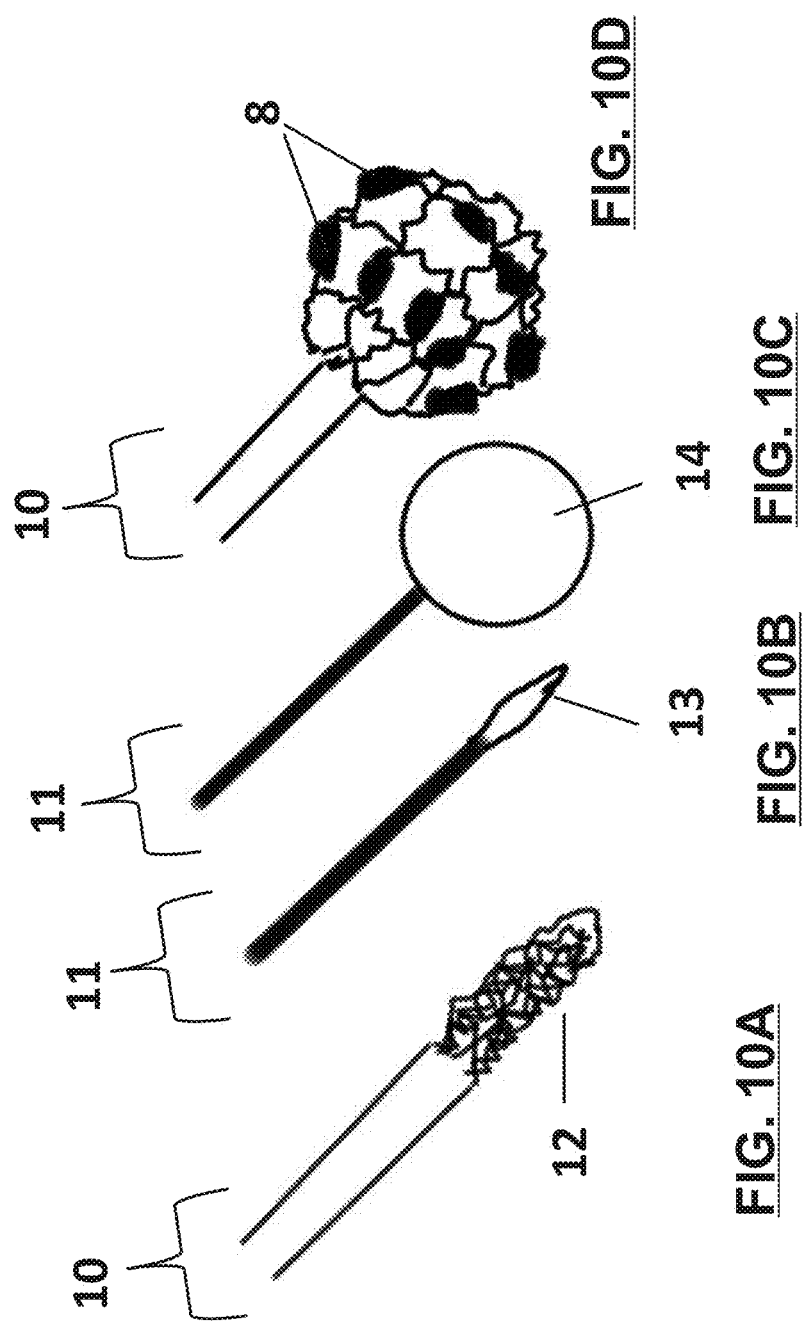
FIGS. 10A-10D illustrate embodiments of an expandable electrode system.

FIGS. 10A-10D illustrate embodiments of an expandable electrode system. FIG. 10A shows an electrode catheter with an expanded mesh tip (12) that is collapsed for safe insertion through brain tissue. FIG. 10B shows a sylet (11) designed to be placed within the lumen of the electrode catheter (10). The expansion mechanism, here being an inflatable balloon (13) is deflated. FIG. 10C shows the expansion mechanism of the inner stylet (11) fully expanded, here being an inflatable balloon. FIG. 10D shows an expandable electrode system that has been fully expanded from the expansion of the expansion mechanism that has now been deflated and withdrawn from the lumen.

Figure 11:
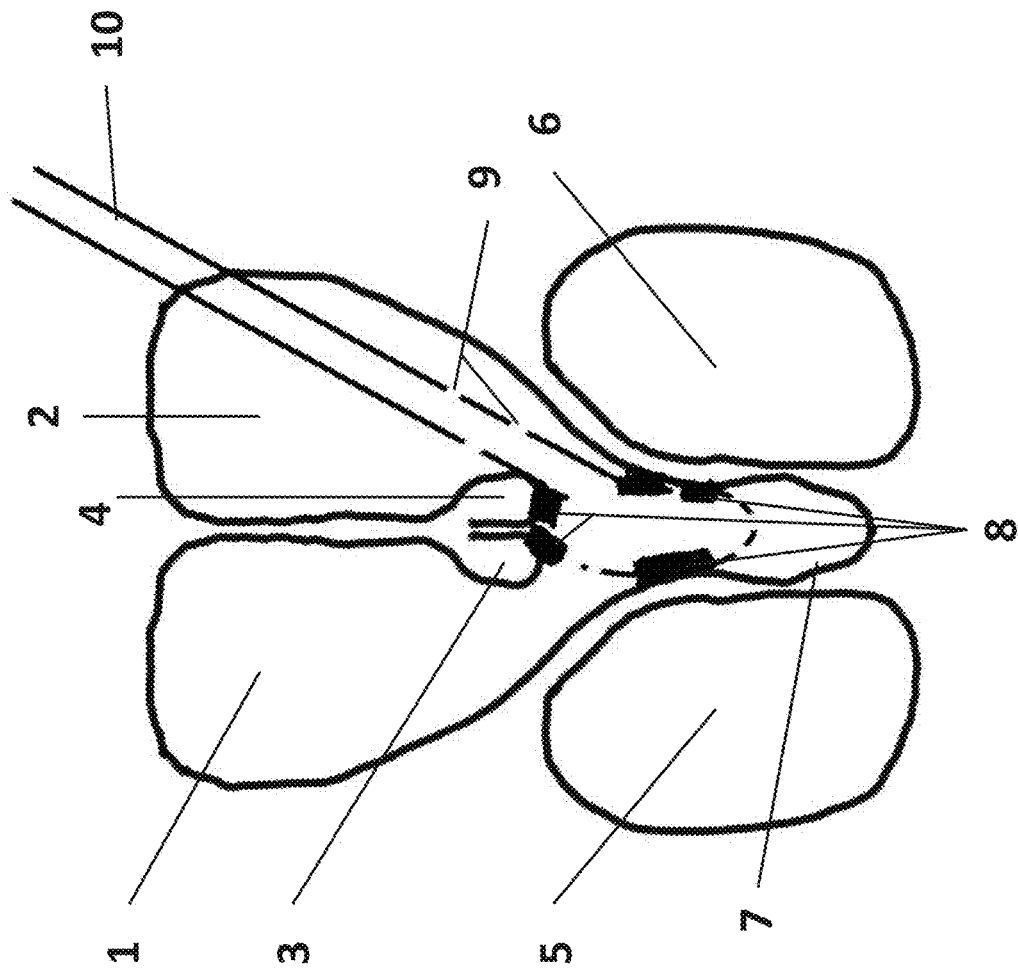
FIG. 11 illustrates an expandable electrode system inserted into the brain.

FIG. 11 illustrates an expandable electrode system (10) showing the electrode catheter (10) passing through the left lateral ventricle (2) through the foramen of Monroe (not labeled) and into the third ventricle (7). The expandable electrode system is expanded (through one of several state of the art techniques including a balloon expansion system shown in FIGS. 10A-10D). The electrodes (8) are positioned on the surface of the mesh to contact the fornices (3, 4) and thalami (5, 6). Perforations or openings in the mesh (9) allow free CSF flow between the ventricular systems.

Figure 12:
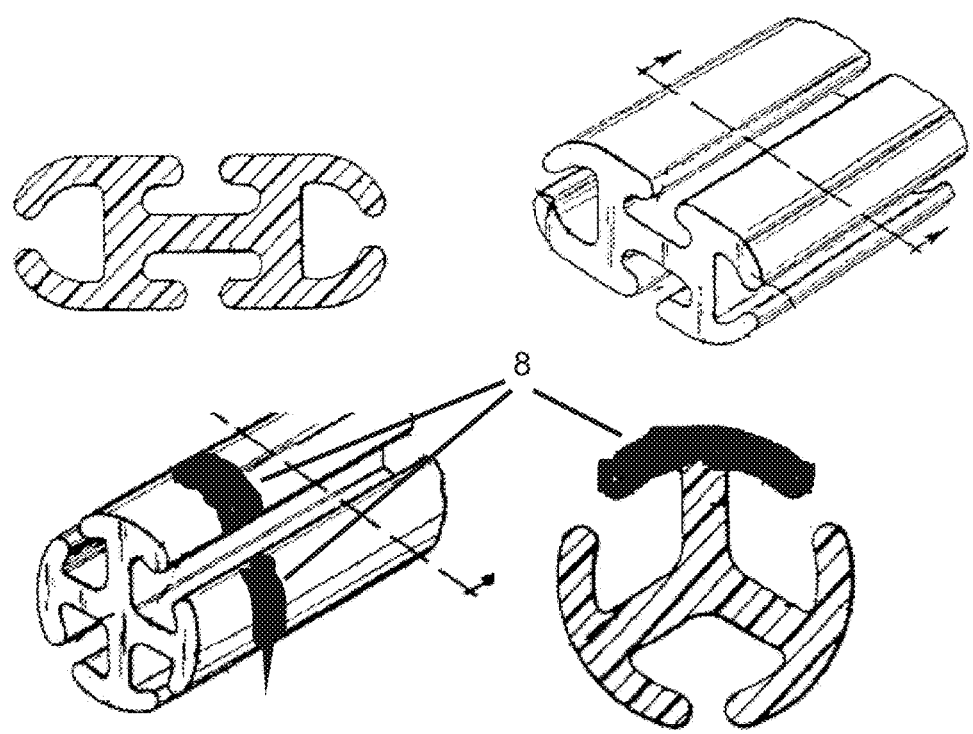
FIG. 12 illustrates examples of Blake drains with embedded electrodes.

FIG. 12 illustrates examples of Blake drains which allow fluid flow through the catheter without a closed lumen. Electrodes (8) are located at the outer surfaces of the drains but can also be located within the inner areas of the catheter for current steering.

In addition to shunt catheters with electrode or effectors within the wall of the shunt catheter, other embodiments are also envisioned. Cardiac stent electrodes have been proposed for intravascular cardiac pacing and defibrillation. These expandable wire mesh electrodes allow blood to run through the mesh electrode while expanding to the wall of the blood vessel to stimulate cardiac pacing structures just outside the vascular wall. This type of mesh electrode system would also work for the cerebral ventricular system where wire mesh electrodes expand to fill the foramen of Monroe and/or the third ventricle. In this manner, bilateral thalamic (Anterior and Dorsal Medial Nuclei) and hypothalamic nuclei can be accessed and modulated. Aside from electrodes designed for cardiac and vascular use, any type of drain used surgically to drain fluid from the body can be used as a passageway for CSF. The type of drains include Blake type drains (see FIG. 12) which do not have an inner and outer surface since geometrically they have a cross sectional shape of a star and the fluid flows in between the arms of the star formation. The effectors or electrodes of this embodiment would be located anywhere along the inside of the drain including the tips of the star but could also have effectors or electrodes in the middle of the star at the junction of the arms so that current can be directed (steered) outwardly from the middle of the catheter outwards towards brain tissue.

Although this invention has been described in terms of certain embodiments, other embodiments that are apparent to those of ordinary skill in the art, including embodiments that do not provide all of the features and advantages set forth herein, are also within the scope of this invention. Moreover, the various embodiments described above can be combined to provide further embodiments. In addition, certain features shown in the context of one embodiment can be incorporated into other embodiments as well. Accordingly, the scope of the present invention is defined only by reference to the appended claims or by claims as presented in the future.

What is claimed is:

1. A neuromodulation system configured to pass into, within, or through brain tissue from a lateral entry site to provide bilateral deep brain stimulation, the system comprising:
   an electrode catheter comprising one or more passageways for fluid, wherein the electrode catheter comprises at least one fluid drainage perforation that is configured to drain fluid through the one or more passageways, wherein the electrode catheter is configured to provide both electrical and drainage capabilities; and
   a plurality of electrodes or effectors carried by the electrode catheter configured for bilateral stimulation and configured to modulate neural activity thereby modulating a neural state, wherein the at least one fluid drainage perforation is located between the plurality of electrodes or effectors;
   wherein the electrode catheter is sized and configured to pass through one lateral ventricle in a unilateral approach through a foramen of Monroe on an ipsilateral side into the third ventricle, and a tip of the electrode catheter is configured to curve under the ipsilateral fornix to the contralateral fornix by curving from the foramen of Monroe on the ipsilateral side past the ipsilateral fornix to the contralateral fornix.

2. The neuromodulation system of claim 1, wherein the neural activity modulated comes from one of more of the following: brain cells, neural fibers, fornix, thalamus, anterior nucleus of thalamus, a structure within the circuit of Papez, and hypothalamus.

3. The neuromodulation system of claim 1, wherein the neural state is one or more of the following neural states: a normal neural state, an abnormal neural state, an abnormal neural state related to seizure, an abnormal neural state related to epilepsy, an abnormal neural state related to Alzheimer's disease, an abnormal neural state related to Mild Cognitive Impairment, an abnormal neural state related to normal pressure hydrocephalus, an abnormal neural state related to Attention Deficit and Hyperactivity Disorder, an abnormal neural state related to encephalopathy, an abnormal neural state related to stroke, an abnormal neural state related to Parkinson's Disease, an abnormal neural state related to neurodegenerative disease, an abnormal neural state related to cerebral palsy, an abnormal neural state related to schizophrenia, an abnormal neural state related to neuropsychiatric disorder.

4. The neuromodulation system of claim 1, wherein the modulation of neural activity comprises one or more of the following: an increase in neural activity, a decrease in neural activity, a modulation of memory, attention, concentration.

5. The neuromodulation system of claim 1, wherein the electrode catheter comprises perforations to permit cerebral spinal fluid to flow therethrough.

6. The neuromodulation system of claim 1, wherein the passageway is configured to permit cerebrospinal fluid to flow out of the cranium to drain into a body cavity including the circulatory system, peritoneum, or pleural space, and wherein the passageway comprises a shunt system with a valve controlling cerebrospinal fluid flow.

7. The neuromodulation system of claim 1, wherein the passageway is configured so as to not be open to cerebrospinal fluid flow outside the cranium.

8. The neuromodulation system of claim 1, wherein the system is configured to allow the electrode or effector to reach both the fornix and anterior nucleus of thalamus.

9. The neuromodulation system of claim 1, wherein the electrode catheter is configured to use mechanical properties to maintain contact with neural structures on the wall of the ventricle or a foramen of Monroe.

10. The neuromodulation system of claim 1, wherein the catheter diameter can be enlarged or decreased to better fit within the ventricle or a foramen of Monroe so that the electrode or effector is in better contact with the neural structures on the wall of the ventricular system.

11. The neuromodulation system of claim 1, wherein the electrode catheter is configured to be inserted to the target using one or more of the following means: stereotactic guidance, an endoscopic viewer, fluoroscopic visualization guided by radio-opaque substance, and ventriculography.

12. The neuromodulation system of claim 1, wherein the electrode catheter is configured to be introduced supratentorially.

13. The neuromodulation system of claim 1, further comprising a straight stylet that is configured to be inserted into the electrode catheter, wherein removal of the straight stylet from the electrode catheter causes the electrode catheter to curve.

14. The neuromodulation system of claim 1, wherein the electrode catheter is configured to be introduced laterally through a burr hole.

15. The neuromodulation system of claim 1, wherein the electrode is shaped to conform to the shape of the lateral ventricle on the ipsilateral side through the foramen of Monroe on the ipsilateral side through the third ventricle through the foramen of Monroe on the contralateral side into the contralateral lateral ventricle.

16. The neuromodulation system of claim 1, wherein the tip of the electrode catheter is configured to curve in a "V" shape.

17. The neuromodulation system of claim 1, comprising electrodes on both sides of a bend in the "V" shape configured to provide bilateral stimulation.

18. The neuromodulation system of claim 1, wherein the at least one fluid drainage perforation is configured to drain fluid out of the cranium.

19. The neuromodulation system of claim 1, wherein the at least one fluid drainage perforation is configured to drain fluid from at least one of the left ventricle, right ventricle, and third ventricle.

20. The neuromodulation system of claim 1, wherein the plurality of electrodes or effectors are directional.

* * * * *